US006878380B2

(12) United States Patent
Farrell et al.

(10) Patent No.: US 6,878,380 B2
(45) Date of Patent: Apr. 12, 2005

(54) COSMETIC EFFERVESCENT CLEANSING PILLOW

(75) Inventors: Linda Farrell, Stratford, CT (US); Craig Stephen Slavtcheff, Guilford, CT (US); Alexander Paul Znaiden, Trumbull, CT (US); Paul Vinski, Danbury, CT (US)

(73) Assignee: Chesebrough-Pond's USA, division of Conopco, Inc., Greenwich, CT (US)

( * ) Notice: Subject to any disclaimer, the term of this patent is extended or adjusted under 35 U.S.C. 154(b) by 240 days.

(21) Appl. No.: 09/950,301

(22) Filed: Sep. 10, 2001

(65) Prior Publication Data

US 2002/0039558 A1 Apr. 4, 2002

Related U.S. Application Data

(62) Division of application No. 09/783,777, filed on Feb. 15, 2001, now Pat. No. 6,610,312, which is a division of application No. 09/532,767, filed on Mar. 22, 2000, now Pat. No. 6,217,854, which is a division of application No. 09/130,981, filed on Aug. 7, 1998, now Pat. No. 6,063,390.

(51) Int. Cl.[7] .......................... A61K 7/06; A61K 7/075; A61K 9/70; A61K 7/50; A61K 31/355
(52) U.S. Cl. ..................... 424/401; 424/70.1; 424/70.9; 424/70.22; 424/400; 424/402; 424/443; 510/130; 510/140; 514/458; 514/474; 514/725; 514/846; 514/975
(58) Field of Search ................................ 424/401, 402, 424/443, 59, 62, 70.1, 70.9, 70.22, 400; 514/458, 725, 474, 846, 975; 510/130, 140

(56) References Cited

U.S. PATENT DOCUMENTS

| | | |
|---|---|---|
| 1,808,834 A | 6/1931 | Busch, Sr. |
| 3,242,093 A | 3/1966 | Compton et al. |
| 4,025,628 A | 5/1977 | Dewey et al. |
| 4,234,442 A | 11/1980 | Cornelissens |
| 4,272,393 A | 6/1981 | Gergely |
| 4,291,685 A | 9/1981 | Taelman |
| 4,311,606 A | 1/1982 | Kaeser |
| 4,515,703 A | 5/1985 | Haq |
| 4,592,855 A | 6/1986 | Gioffre et al. |
| 4,600,620 A | 7/1986 | Lloyd et al. |
| 4,601,938 A | 7/1986 | Deacon et al. |
| 4,603,069 A | 7/1986 | Haq et al. |
| 4,643,939 A | 2/1987 | Sugiyama et al. |
| 4,666,707 A | 5/1987 | Eguchi et al. |
| 4,745,021 A | 5/1988 | Ping, III et al. |
| 4,791,097 A | 12/1988 | Walele et al. |
| 4,808,322 A | 2/1989 | McLaughlin |
| 4,852,201 A | 8/1989 | Wundrock et al. |
| 4,886,387 A | 12/1989 | Goldberg et al. |
| 4,941,990 A | 7/1990 | McLaughlin |
| 4,946,617 A | 8/1990 | Sheridan et al. |
| 5,006,339 A | 4/1991 | Bargery et al. |
| 5,026,551 A | 6/1991 | Yorozu et al. |
| 5,041,233 A | 8/1991 | Kutny et al. |
| 5,091,102 A | 2/1992 | Sheridan |
| 5,094,770 A | 3/1992 | Sheridan et al. |
| 5,100,674 A | 3/1992 | Ser et al. |
| 5,198,198 A | 3/1993 | Gladfelter et al. |
| 5,306,439 A | 4/1994 | Lockhart |
| 5,338,476 A | 8/1994 | Pancheri et al. |
| 5,342,535 A | 8/1994 | Ramirez et al. |
| 5,352,387 A | 10/1994 | Rahman et al. |
| 5,431,841 A | 7/1995 | Lockhart |
| 5,560,873 A | 10/1996 | Chen et al. |
| 5,578,562 A | 11/1996 | Lockhart |
| 5,605,749 A | 2/1997 | Pike et al. |
| 5,607,681 A | 3/1997 | Galley et al. |
| 5,683,976 A | 11/1997 | Colurciello, Jr. et al. |
| 5,714,451 A | 2/1998 | Brouwer et al. |
| 5,718,729 A | 2/1998 | Harris |
| 5,720,949 A | 2/1998 | Davis |
| 5,804,546 A | 9/1998 | Hall |
| 5,955,057 A | 9/1999 | Maunder et al. |
| 6,063,390 A | 5/2000 | Farrell et al. |
| 6,093,218 A | 7/2000 | Hall et al. |
| 6,103,644 A | 8/2000 | Sheridan |
| 6,121,215 A | 9/2000 | Rau |
| 6,153,208 A * | 11/2000 | McAtee et al. ............. 424/402 |
| 6,190,678 B1 * | 2/2001 | Hasenoehrl et al. ........ 424/401 |
| 6,280,757 B1 | 8/2001 | McAtee et al. |
| 6,338,855 B1 * | 1/2002 | Albacarys et al. .......... 424/409 |
| 6,451,331 B1 * | 9/2002 | Slavtcheff et al. .......... 424/404 |
| 6,491,928 B1 * | 12/2002 | Smith, III ................... 424/401 |

FOREIGN PATENT DOCUMENTS

| | | |
|---|---|---|
| DE | 19745964 | 12/1996 |
| EP | 343070 | 5/1989 |
| EP | 343069 | 11/1989 |
| EP | 0 353 014 A2 * | 1/1990 |
| EP | 423015 | 4/1991 |
| EP | 0 806 201 | 5/1996 |
| FR | 2 196 632 * | 3/1974 |
| GB | 2 118 961 | 4/1982 |
| JP | 62045519 | 2/1987 |
| JP | 10245075 | 9/1998 |
| WO | 97/43366 | 11/1997 |
| WO | 98/42303 | 10/1998 |

OTHER PUBLICATIONS

International Search Report, Oct. 11, 1999.

* cited by examiner

*Primary Examiner*—Marina Lamm
(74) *Attorney, Agent, or Firm*—Milton L. Honig

(57) ABSTRACT

A wiping article is provided which includes an effervescent cleanser composition held within a pouch formed from a first and second substrate sheet. At least one of the substrate sheets must be water permeable. The effervescent composition is an intimate mixture of an acid material such as citric acid and an alkaline material such as sodium bicarbonate. Water contact causes the combination to effervesce. A dry surfactant such as sodium cocoyl isethionate in contact with the water and effervescing carbon dioxide results in a highly pleasant sudsing system. Skin benefit agents may be included within the composition. The effervescent action may improve deposition of the skin benefit agents onto the skin.

14 Claims, No Drawings

COSMETIC EFFERVESCENT CLEANSING PILLOW

This is a Divisional of U.S. patent application Ser. No. 09/783,777 filed Feb. 15, 2001, U.S. Pat. No. 6,610,312, which is a Divisional of Ser. No. 09/532,767 filed Mar. 22, 2000, granted as U.S. Pat. No. 6,217,854, which is a Divisional of Ser. No. of 09/130,981 filed Aug. 7, 1998, granted as U.S. Pat. No. 6,063,390.

BACKGROUND OF THE INVENTION

1. Field of the Invention

The invention concerns an effervescent foaming wipe article for body cleansing that imparts a pleasant sensory feel to a user's skin.

2. The Related Art

Classically the process of cleansing skin or other articles has employed a surfactant composition. Sometimes an implement has joined the composition. Implements such as sachets serve a multi-purpose. One function is as a delivery package for the surfactant. Sachets may also assist in generating foam. They also function as an abrasive assisting in the cleansing function.

An early example of cleansing pad technology is found in U.S. Pat. No. 1,808,834 (Busch Sr.). A fabric pouch is disclosed surrounding a cleansing composition mainly consisting of calcium and sodium carbonate.

U.S. Pat. No. 4,234,442 (Cornelissens) describes a sachet which can consist of a water permeable material filled with an acidic and an alkaline constituent. Adipic, succinic and glutaric acids exemplify the acidic constituent. Sodium bicarbonate and carbonate represent the alkaline ingredient.

U.S. Pat. No. 4,272,393 (Gergely) describes a cleaning article formed of a porous flexible substrate, especially a cellulosic paper, impregnated with detergent and a gas-generating system. The latter is formed by separating an acidic component such as citric acid from a basic component such as sodium carbonate in two separate areas of the substrate.

U.S. Pat. No. 4,515,703 (Haq), U.S. Pat. No. 4,600,620 (Lloyd et al.) and U.S. Pat. No. 4,603,069 (Haq et al.) all describe wiping articles impregnated with surfactant. These do not contain any effervescent ingredients.

WO 97/43366 (Askew et al.) reports an effervescent system to improve dispensability of granular laundry detergent powders into wash water of automatic washing machines. Citric acid and bicarbonate combinations are employed to generate effervescence.

It is an object of the present invention to provide a cleansing cloth containing an effervescent system activated by contact with water.

Another object of the present invention is to provide a cleansing cloth containing an effervescent system activated by contact with water to generate carbon dioxide which expands the lathering of cleanser components of the cloth.

Still a further object of the invention is to provide a cleansing cloth which imparts a pleasant sensory feel to skin during and after use.

It is to be noted that the subsequently described invention is broader than the objects or technical problems it is directed to solve.

SUMMARY OF THE INVENTION

A cosmetic article is provided for cleansing body surfaces, the article including:

- a pouch formed of first and second sheets, at least one being water permeable, the first and second sheets defining a pouch between them, the pouch being sealed along all its perimeter; and
- an effervescent cleanser composition in the form of an anhydrous dry solid being positioned within the pouch, the composition including:
  - (i) from about 1 to about 80% of an alkaline material,
  - (ii) from about 0.5 to about 80% of an acid material; and
  - (iii) from about 0.1 to about 30% of a solid surfactant.

Also provided is a method for cleansing skin involving wetting with water a cosmetic cleansing article, generating foam from the article and wiping skin surfaces with the wetted article, the article being the pouch with effervescent cleanser composition delineated above.

DETAILED DESCRIPTION OF THE INVENTION

Cosmetic wiping articles of the present invention when contacted with water billow to many times (more than 10 but often more than 40 times) their dry size when activated by water. The effervescent cleansing system exudes copious amounts of lather. A plumped "pillow" arises from the effervescent action. By careful control of the acidic and alkaline components, a squeaky clean rinsed feeling is felt on a user's skin.

A first essential component of compositions within the pouch is that of an acidic material. Suitable for this purpose are any acids present in dry solid form. Especially appropriate are $C_2$–$C_{20}$ organic mono- and poly-carboxylic acids and especially alpha- and beta-hydroxycarboxylic acids: $C_2$–$C_{20}$ organophosphorus acids such as phytic acid; $C_2$–$C_{20}$ organosulfur acids such as toluene sulfonic acid; and peroxides such as hydrogen peroxide. Typical hydroxycarboxylic acids include adipic, glutaric, succinic, tartaric, malic, maleic, lactic, salicylic and citric acids as well as acid forming lactoses such as gluconolactone and glucarolactone. Most preferred is citric acid. Also suitable as acid material may be encapsulated acids. Typical encapsulating material may include water soluble synthetic or natural polymers such as polyacrylates (e.g. encapsulating polyacrylic acid), cellulosic gums, polyurethane and polyoxyalkylene polymers. By the term "acid" is meant any substance which when dissolved in deionized water at 1% concentration will have a pH of less than 7, preferably less than 6.5, optimally less than 5. These acids preferably at 25° C. are in solid form, i.e. having melting points no less than 25° C. Concentrations of the acid should range from about 0.5 to about 80%, preferably from about 10 to about 65%, optimally from about 20 to about 45% by weight of the total composition.

A second essential component of compositions within the pouch is that of an alkaline material. The alkaline material is a substance which can generate a gas such as carbon dioxide, nitrogen or oxygen, i.e. effervesce, when contacted with water and the acidic material. Suitable alkaline materials are anhydrous salts of carbonates and bicarbonates, alkaline peroxides (e.g. sodium perborate and sodium percarbonate) and azides (e.g. sodium azide). Preferably the alkaline materials sodium or potassium bicarbonate. Amounts of the alkaline material may range from about 1 to about 80%, preferably from about 5 to about 49%, more preferably from about 15 to about 40%, optimally from about 25 to about 35% by weight of the total composition.

By the term "anhydrous" is meant the presence of no more than 5%, preferably no more than 3.5% and optimally no more than 1% water by weight of the total composition. Water of hydration is not considered to be water for purposes of the anhydrous definition. However, it is preferred to minimize, preferably to eliminate any water of hydration.

Advantageously the combined amount of acidic and alkaline materials will be at least about 1.5%, preferably from about 40 to about 95%, optimally from about 60 to about 80% by weight of the total composition.

A third necessary component of compositions according to the present invention is that of a dry surfactant, preferably a dry surfactant solid at 20° C. Most suitable for the present invention is sodium cocoyl isethionate. Other useful surfactants include sodium methyl cocoyl taurate and sodium lauryl sulfate. Surfactants may be of the anionic, cationic, nonionic, amphoteric, zwitterionic varieties and combinations thereof. Amounts of the dry surfactant may range from about 0.1 to about 30%, preferably from about 1 to about 30%, optimally from about 8 to about 15% by weight of the total composition.

A variety of skin benefit agents may be included to improve afterfeel properties. Advantageously these substances will be available as anhydrous dry powders. Alternatively these substances may be liquids deposited upon or into a powdered substrate (e.g. sodium bicarbonate or zeolite) to achieve a resultant dry flowing powder. Within the skin benefit agent scope are several categories of materials. These include emollients, antiaging actives, antibacterials and fungicides, skin lighteners, sunscreens and combinations thereof. Amounts of the skin benefit agents may range from about 0.001 to about 30%, preferably from about 0.1 to about 20%, more preferably from about 0.5 to about 10%, optimally between about 1 and about 5% by weight of the total composition.

Emollients may be in the form of natural or synthetic esters, silicone oils, hydrocarbons, starches, fatty acids and mixtures thereof. Typically the emollient may range in concentration from about 0.1 to about 35% by weight of the total composition.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes; polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid ester, diethylene glycol mono- and di-fatty acid esters, polyethylene glycol (200–6000) mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

(6) Triglycerides such as sunflower seed oil, maleated sunflower seed oil, borage seed oil and safflower oil.

Hydrocarbons suitable as emollients include petrolatum, mineral oil, isoparaffins and hydrocarbon waxes such as polyethylene.

Starches are also suitable emollients. Typical of this class is tapioca and arabinogalactan.

Fatty acids may also be suitable as emollients. The fatty acids normally have from 10 to 30 carbon atoms. Illustrative of this category are pelargonic, lauric, myristic, palmitic, stearic, isostearic, hydroxystearic, oleic, linoleic, riconleic, arachidic, behenic and erucic acids.

Antiaging actives are also useful as skin benefit agents. Included within this category are vitamins, retinoids and combinations thereof. Amounts of these materials may range from about 0.001 to about 20% by weight of the total composition. Suitable vitamins include ascorbic acid, Vitamin $B_6$, Vitamin $B_{12}$, tocopherol as well as salts and $C_1$–$C_{20}$ esters thereof. Suitable retinoids include retinoic acid as well as its $C_1$–$C_{22}$ esters and salts, retinol and $C_1$–$C_{22}$ fatty esters of retinol including retinyl linoleate.

Another class of antiaging actives are the alpha- and beta-hydroxycarboxylic acids and salts thereof. Representative of this group are glycolic acid, lactic acid, malic acid, hydroxyoctanoic acid and mixtures of these as well as their salts. Suitable salts are the alkalimetal, ammonium and $C_1$–$C_{10}$ alkanol ammonium salts.

Antibacterials and fungicidals may also be included as skin benefit agents. Representative of these categories are triclosan, tricloban, hexetidene, chlorhexadene, gluconates, zinc salts (e.g. zinc citrate and zinc phenolsulfonate) and combinations thereof.

Skin lighteners may also be included under the skin benefit agents. Typical of this category are niacinamide, kojic acid, arbutin, vanillin, ferulic acid and esters thereof, resorcinol, hydroquinone, placental extract and combinations thereof.

Sunscreens may also be included as skin benefit agents. Particularly preferred are such materials as ethylhexyl p-methoxycinnamate, available as Parsol® MCX, and benzophenone-3, also known as Oxybenzone. Inorganic sunscreen actives may be employed such as microfine titanium dioxide, polyethylene and various other polymers. Amounts of the sunscreen agents will generally range from 0.1 to 30%, preferably from 2 to 20%, optimally from 4 to 10% by weight.

Adjunct functional agents may also be incorporated into compositions of the present invention. These include electrolytes, thickeners and mixtures thereof. Amounts of these substances may range from about 0.1 to about 20%, preferably from about 0.3 to about 10%, optimally between about 0.5 and about 5% by weight of the total composition.

Electrolytes may be selected from alkali, alkaline earth or ammonium salts of phosphates, silicates, halides, sulphates and mixtures thereof. Typical phosphates are potassium polymetaphosphate, sodium tripolyphosphate, sodium tetrapyrophosphate, sodium or potassium pyrophosphate and sodium hexametaphosphate. Most preferred is potassium polymetaphosphate available as Lipothix 100B® which is a 70:30 mixture of potassium polymetaphosphate and sodium bicarbonate, available from Lipo Chemicals, Inc., Paterson, N.J. Preferred sulphates are the magnesium sulphates.

Thickeners which may improve afterfeel properties on skin include inorganic or organic substances. A particularly preferred inorganic thickener is sodium magnesium silicate commercially available as Optigel SH®. Organic thickeners include alginic acid as well as sodium and calcium alginates, sodium carboxymethyl cellulose, hydroxypropyl methylcellulose, hydroxypropyl cellulose, hydroxyethyl cellulose and combinations thereof. Most preferred is alginic acid commercially available as Kelacid® from Sud-Chemie Rheologicals, Louisville, Ky. Alginic acid is highly effective at removing the slimy feel associated with deposits of alkaline material which are not fully rinsed away from the skin. Amounts of the thickener may range from about 0.1 to about 20%.

Polysaccharides useful in this invention are dry solid anhydrous substances such as sorbitol, sugars, (such as trehalose) starches, modified starches (e.g. aluminum octenyl succinate) and mixtures thereof. Most preferred is sorbitol.

Deposition aids may also be incorporated in compositions of the present invention. These assist in depositing skin benefit agents onto the skin surface. Particularly effective are cationic monomers and polymers for this purpose. Illustrative are the following:

Lauryltrimethylammonium chloride (Laurtrimonium chloride);
Stearyltri(2-hydroxyethyl)ammonium chlorine (Quaternium-16);
Lauryldimethylbenzylammonium chloride (Lauralkonium chloride);
Oleyldimethylbenzlammonium chloride (Olealkonium chloride);
Dilaurylaimethylammonium chloride (Dilaurylaimonium chloride);
Cetyldimethylbenzylammonium chloride (Cetalkonium chloride);
Dicetyldimethylammonium chloride (Dicetyldimonium chloride);
Laurylpyridinium chloride (Laurylpyridinium chloride);
Cetylpyridinium chloride (Cetylpyridinium chloride);
N-(soya alkyl)-N,N,N-trimethylammonium chloride (Soyatrimonium chloride);
Polydiallyldimethylammonium chloride (Polyquaternium-6);
Diallydimethylammonium salt copolymerized with acrylamide (Polyquaternium-7);
Guar hydroxypropyltrimonium chloride (Guar hydroxypropyl-trimonium chloride);
Copolymer of N-vinyl-pyrrolidone and N,N-dimethylaminoethylmethacrylate, quaternized with dimethylsulfate (Polyquaternium-11);
Copolymer of acrylamide and N,N-dimethylaminoethyl methacrylate, quaternized with dimethyl sulfate (Polyquaternium-5);
Cationic hydroxyethylcellulosics (Polyquaternium-10);
Cationic hydroxyethylcellulosics (Polyquaternium-24);
Cetyltrimethylammonium chloride (Cetrimonium chloride);
Decyldimethyloctylammonium chloride (Quaternium-24);
Myristytrimethylammonium chloride (Mytrimonium chloride);
Polyoxyethylene (2)-cocomonium chloride (PET-2 Cocomonium chloride);
Methylbis(2-hydroxyethyl)cocoammonium chloride (PEG-2 Cocoyl Quaternium-4);
Methylpolyoxyethylene-(15) (PEG-15 Cocoyl cocoammonium chloride Quaternium-4);
Methylbis (2-hydroxyethyl) octadecyl ammonium chloride (PEG-2 Stearyl Quaternium-4);
Methylpolyoxyethylene-(15) octadecylammonium chloride (PEG-15 Stearyl Quaternium-4);
Methylbis(2-hydroxyethyl)-oleylammonium chloride (PEG-2 Oleyl Quaternium-4);
Methylpolyoxyethylene-(15)oleylammonium chloride (PEG-15 Oleyl Quaternium-4);

The names in parenthesis are given by the Cosmetic, Toiletry and Fragrance Association, Inc. in the CTFA Cosmetic Ingredient Dictionary. Most preferred for purposes of this invention are cationic guar gums such as Jaguar C13S® which is guar hydroxyproplytrimonium chloride. Amounts of the deposition aid may range from about 0.01 to about 1%, preferably from about 0.05 to about 0.5%, optimally from about 0.1 to about 0.3% by weight.

Advantageously an emotive agent such as a fragrance and/or botanical extract are included with the effervescent cleansing composition. Fragrances and botanicals are often liquids. For this reason it is necessary to uniformly distribute and allow absorption of liquid components into the solid powder. One method of best achieving this is to spray these liquids onto the solids. Amounts of the fragrance and/or botanicals combined may be at levels from abut 0.1 to about 3%, preferably from 0.5 to 2%, optimally from 0.8 to 1.5% by weight of the total composition.

The term "fragrance" is defined as a mixture of odoriferous components, optionally mixed with a suitable solvent diluent or carrier, which is employed to impart a desired odor. Particular preferred odoriferous components are cyclic and acyclic terpenes and terpenoids. These materials are based upon isoprene repeating units. Examples include alpha and beta pinene, myrcene, geranyl alcohol and acetate, camphene, di-limonene, alpha and beta phellandrene, tricyclene, terpinolene, allocimmane, geraniol, nerol, linanool, dihydrolinanool, citral, ionone, methyl ionone, citronellol, citronellal, alpha terpineol, beta terpineol, alpha fenchol, borneol, isoborneol, camphor, terpinen-1-ol, terpin-4-ol, dihydroterpineol, methyl chavicol, anethole, 1,4 and 1,8 cineole, geranyl nitrile, isobornyl acetate, linalyl acetate, caryophyllene, alpha cedrene, guaiol, patchouli alcohol, alpha and beta santalol and mixtures thereof. Botanicals of particular use in the present invention include yarrow, chamomile, jasmine, lavender, horse chestnut, sage, thyme, yucca, coltsfoot and mixtures thereof.

Preservatives can desirably be incorporated into the cosmetic compositions of this invention to protect against the growth of potentially harmful microorganisms. Suitable traditional preservatives for compositions of this invention are alkyl esters of para-hydroxybenzoic acids. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl acraben, imidazolidinyl urec, sodium dehydroacetate and benzyl alcohol. The preservatives should be selected having regard for the sue of the composition and possible incompatibilities between the preservatives and other ingredients in the emulsion. Preservatives are preferably employed in amounts ranging from 0.01% to 2% by weight of the composition.

Natural vegetable materials from renewable resources are often desirable in cosmetic compositions. For instance, cosmetic compositions of the present invention may include beta-glucan derived from oats, commercially available under the trademark Microat SF from Nurture Inc., Missoula, Mont.

Colorants may also be included in compositions of the present invention. These substances may range from about 0.05 to about 5%, preferably between 0.1 and 3% by weight.

Effervescent cleansing compositions of this invention will be placed within a pouch formed between a first and second flexible substrate sheet, preferably at least one of these being a flexible sheet. At least one of the sheets must be water permeable, most preferably both sheets should have water permeability. For definitional purposes, first and second sheets can be folded-over panels of a single unitary sheet. Suitable materials for forming sheets may be rayon, polyester, polyethylene, polypropylene, cotton or any combination thereof. These sheets may be woven or non-woven. Most preferred is a non-woven rayon. Cellulosic paper fiber substrates are best not employed because of their insufficient wet-strength although they may be blended with other fibers referenced above; it is important that the substrate sheets are not readily torn open through consumer rubbing of the article. Unlike laundry sachet articles, pouches of the present invention should not rupture to allow dispersion of their granular contents into wash water. Rather it is intended for all cleanser composition components to exit by dissolution through the permeable walls of the pouch.

Skin surfaces against which articles of the present invention are useful include face, body, scalp, axilla and even legs/feet. When the article is a foot cleanser, it would be advantageous for the pouch for the pouch on one of its sides to be coarse while the second of the sheets may be soft and gentle. An abrasive non-woven flexible sheet in a foot cleanser product is useful for rubbing against calluses while the second sheet of the pouch remains smooth.

Articles according to the present invention may be formed in the following manner. Constituents of the effervescent cleansing composition are placed into a dry mill or similar apparatus and blended until a uniformally distributed powder results. Thereafter, fragrance/botanical component as a Phase B is sprayed into the dry mill with concurrent agitation of the powdered composition.

A continuous roll of first substrate sheet is unwound from a source roll over a moving conveyer belt. The effervescent cleansing composition is placed into a hopper positioned over the conveyer belt. A discrete charge of powdered composition is regularly placed on the first substrate sheet. At a location directly under a nozzle of the hopper. A second substrate sheet is then in register placed over that of the loaded first substrate sheet. At this point all four corners defining a rectangle or square are sealed in register trapping the effervescent cleansing composition within. Cutters then separate one sealed section from another thereby forming the wiping article. One or more of the wiping articles are then packaged within a moisture impermeable outer package such as a laminated foil bag to prevent activation of the effervescent system during storage.

Ultrasonic welding may be employed as an alternative to heat-sealing of the first and second substrates together. Thread stitching, glue application or other closure mechanisms may also be utilized.

Except in the operating and comparative examples, or where otherwise explicitly indicated, all numbers in this description, indicating amounts of material are to be understood as modified by the word "about".

The term "comprising" is meant not to be limiting to any subsequently stated elements but rather to encompass non-specified elements of major or minor functional importance. In other words the listed steps, elements or options need not be exhaustive.

The following examples will more fully illustrate embodiments of this invention. All parts, percentages and proportions referred to herein and in the appended claims are by weight unless otherwise indicated.

EXAMPLE 1

An effervescent cleansing composition was prepared according to the formulation reported in Table I. Phase A was dry blended in a high speed shearing mixer. Fragrance was then sprayed onto the resultant powder as a Phase B. Three grams of the resultant powder were then placed into a two inch by three inch pouch formed of non-woven rayon. All sides were closed by double stitching with thread.

TABLE I

| INGREDIENT | WEIGHT % |
| --- | --- |
| PHASE A | |
| Sodium Bicarbonate | 34.5 |
| Citric Acid (Anhydrous) | 40.4 |
| Sodium Cocoyl Isethionate (Powder) | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 1.0 |

EXAMPLE 2

Another effervescent cleansing composition was prepared according to the formulation reported in Table II.

TABLE II

| INGREDIENT | WEIGHT % |
| --- | --- |
| PHASE A | |
| Sodium Bicarbonate | 32.3 |
| Citric Acid (Anhydrous) | 41.1 |
| Sodium Cocyl Isethionate (Powder) | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| Laracare A200 ® (Arabinogalactan) | 1.0 |
| Ascorbic Acid | 0.5 |
| PHASE B | |
| Fragrance | 1.0 |

EXAMPLE 3

A face cleansing effervescent composition was prepared according to the formulation reported in Table III.

TABLE III

| INGREDIENT | WEIGHT % |
|---|---|
| PHASE A | |
| Sodium Bicarbonate | 33.6 |
| Citric Acid (Anhydrous) | 39.0 |
| Sodium Cocyl Isethionate (Powder) | 3.0 |
| Sodium Methyl Cocoyl Taurate | 6.0 |
| Sodium Lauryl Sulfate | 2.5 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 2.0 |
| Tapioca | 5.5 |
| Methyl Gluceth 20-Benzoate | 2.0 |
| Guar Hydroxypropyl Trimonium Chloride | 0.25 |
| PHASE B | |
| Fragrance | 0.65 |

EXAMPLE 4

A still further effervescent cleansing composition according to the present invention may be prepared according to the formulation reported under Table IV. Phase A is prepared by dry mixing of the ingredients in a high speed shear mixer. Three grams of resultant powder are placed into a two inch by three inch pouch formed of non-woven cotton polyester (50:50). The mesh size of the pouch walls is sufficient to allow transfer of dissolved ingredients. All sides of the pouch are welded by ultrasonic heat to insure against powder escaping from the pouch.

TABLE IV

| INGREDIENT | WEIGHT % |
|---|---|
| PHASE A | |
| Potassium Bicarbonate | 29.5 |
| Lactic Acid (Anhydrous) | 45.4 |
| Sodium Sulfosuccinate | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 1.0 |
| Licorice Extract | 0.1 |

EXAMPLE 5

Still another effervescent cleansing composition is prepared according to the formulation reported in Table V. The ingredients are dry blended in a high speed shearing mixer. Fragrance and herbal extract are sprayed onto the powder and further blended to achieve homogeneity. Three grams of the resultant powder are placed into a two inch by three inch pouch formed of non-woven polypropylene. All sides are closed by convection heat sealing along the perimeter thereof.

TABLE V

| INGREDIENT | WEIGHT % |
|---|---|
| PHASE A | |
| Sodium Bicarbonate | 29.5 |
| Citraconic Acid (Anhydrous) | 45.4 |
| Methyl Glucamide | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 0.9 |
| Yarrow | 0.1 |

The foregoing description and examples illustrate selected embodiments of the present invention. In light thereof variations and modifications will be suggested to one skilled in the art, all of which are within the spirit and purview of this invention.

What is claimed is:

1. A cosmetic pillow having no more than 5% water and from about 0.1 to about 30% surfactant each by weight of a composition present therein for cleansing body surfaces, the pillow being plumped by effervescent generated carbon dioxide and exuding lather and an emollient when contacted with water.

2. The pillow according to claim 1 wherein the effervescent generated carbon dioxide, exuding lather and emollient arise from the composition held within the pillow.

3. The pillow according to claim 1 wherein he effervescent generated carbon dioxide, the exuded lather and the emollient arise from the composition stored within the pillow, the composition further comprising from about 1 to about 80% of an alkaline material, from about 0.5 to about 80% of an acid material and from 0.01 to about 30% of an emollient by weight of the composition, the composition having no more than 3.5% water.

4. The pillow according to claim 1 wherein the emollient is selected from the group consisting of natural or synthetic esters, silicon oils, hydrocarbons, starches, fatty acids and mixtures thereof.

5. The pillow according to claim 1 wherein the emollient is petrolatum.

6. The pillow according to claim 1 wherein the lather is generated from a surfactant selected from the group consisting of anionic, cationic, nonionic, amphoteric, zwitterionic varieties and combinations thereof.

7. The pillow according to claim 1 wherein the composition comprises no more than 1% water by weight of the composition.

8. The pillow according to claim 1 wherein the composition is anhydrous.

9. The pillow according to claim 1 wherein the composition further comprises a $C_1$–$C_{20}$ ester of tocopherol.

10. The pillow according to claim 3 wherein the alkaline material is sodium bicarbonate and the acid material is citric acid.

11. The pillow according to claim 1 wherein the composition further comprises a botanical extract.

12. The pillow according to claim 11 wherein the extract is chamomile extract.

13. The pillow according to claim 1 wherein the composition further comprises a polyquaternium compound.

14. The pillow to according to claim 1 wherein the composition further comprises a preservative selected from the group consisting of phenoxyethanol, methyl paraben, propyl paraben and mixtures thereof.

* * * * *